United States Patent [19]
Cambiaso et al.

[11] Patent Number: 4,829,012
[45] Date of Patent: May 9, 1989

[54] METHOD FOR IMMUNOLOGICAL ASSAY OF ANTIBODIES OF VARIOUS TYPES IN A LIQUID SAMPLE

[75] Inventors: César L. Cambiaso, Kraainem; Pierre L. Masson, Brussels, both of Belgium

[73] Assignee: L'Association Internationale àbut Scientifique, dite: "Institut International de Pathologie Cellulaire et Moléculaire", Woluwé-Saint-Lambert, Belgium

[21] Appl. No.: 821,441

[22] Filed: Jan. 22, 1986

[30] Foreign Application Priority Data

Jan. 24, 1985 [BE] Belgium .............................. 0/214388

[51] Int. Cl.[4] ................ G01N 33/563; G01N 33/053; G01N 33/557; G01N 33/537
[52] U.S. Cl. ...................................... 436/512; 435/7; 436/513; 436/517; 436/520; 436/538
[58] Field of Search ............... 436/512, 513, 520, 533, 436/517, 825; 435/7

[56] References Cited

U.S. PATENT DOCUMENTS 3,600,494  8/1971  Tumizawa et al. ............. 436/511 X
4,204,837  5/1980  Sternberg et al. ................... 436/517
4,434,227  2/1984  Unger ................................... 436/513

FOREIGN PATENT DOCUMENTS 0101166  6/1983  European Pat. Off. .
2001171  1/1979  United Kingdom .

OTHER PUBLICATIONS

Masson et al., "Particle Counting Immunoassay", *Methods in Enzymology*, vol. 74, pp. 106–139, (1981).
Sites et al., "Agglutenation", *Basic and Clinical Immunology*, 5th Edition, pp. 343–346, (1984).
Henry, J. B., *Clinical Diagnosis and Management by Laboratory Methods*, 16th Ed., W. B. Saunders, Philadelphia, 1979, p. 894.
Organon Teknika NV, "Toxonostika IgM & IgG Microelisa System," (English Translation).
P. L. Masson; Journal of Pharmaceutical & Biomedical Analysis, vol. 5, No. 2, pp. 113–117, 1987; Particle Counting Immunoassay–An Overview.
Galanti et al.; Journal of Virological Methods, vol. 18, (1987), pp. 215–224; Immunoassay of Hepatitis B Surface Antigen by Particle Counting after Pepsin Digestion.
Borque et al.; Clinical Chemistry; vol. 33, pp. 704–707, (1987); Immunoassay of Rheumatoid Factory by Latex Particle Counting.
Chantler and Diment, "Current Status of Specific IgM Antibody Assays", (1981), 417.
Coombs et al., *Lancet*, (1968), 2, 1115.
Gispen et al., (Clin. Esp. Immunology, 1975), 22.
Cerottini et al., J. Immunology, (1968), 101,433.
J. Clin. Microbiology, (1983), voo. no. 17, no. 5, 939.
Westphal et al., Method in Carbiohydrate Chemistry, vol. 5, (1965), p. 83, Academic Press, N.Y.
Moreno et al., J. Bacteriology, (1979), 361, vol. 138, No. 2.

*Primary Examiner*—Robert J. Warden
*Assistant Examiner*—Carol A. Spiegel
*Attorney, Agent, or Firm*—Cushman, Darby & Cushman

[57] ABSTRACT

A method for immunological assay of IgM antibodies against at least one said antigen in a liquid sample containing at least IgM and IgG antibodies, such as a biological fluid, comprising reaction of said liquid sample and of antibodies against IgG, and addition to the so obtained reaction product of the said antigen bound to finely divided particles and of a free said antigen, the amount of IgM being inversely proportional to the amount of unagglutinated finely divided particles.

13 Claims, 4 Drawing Sheets

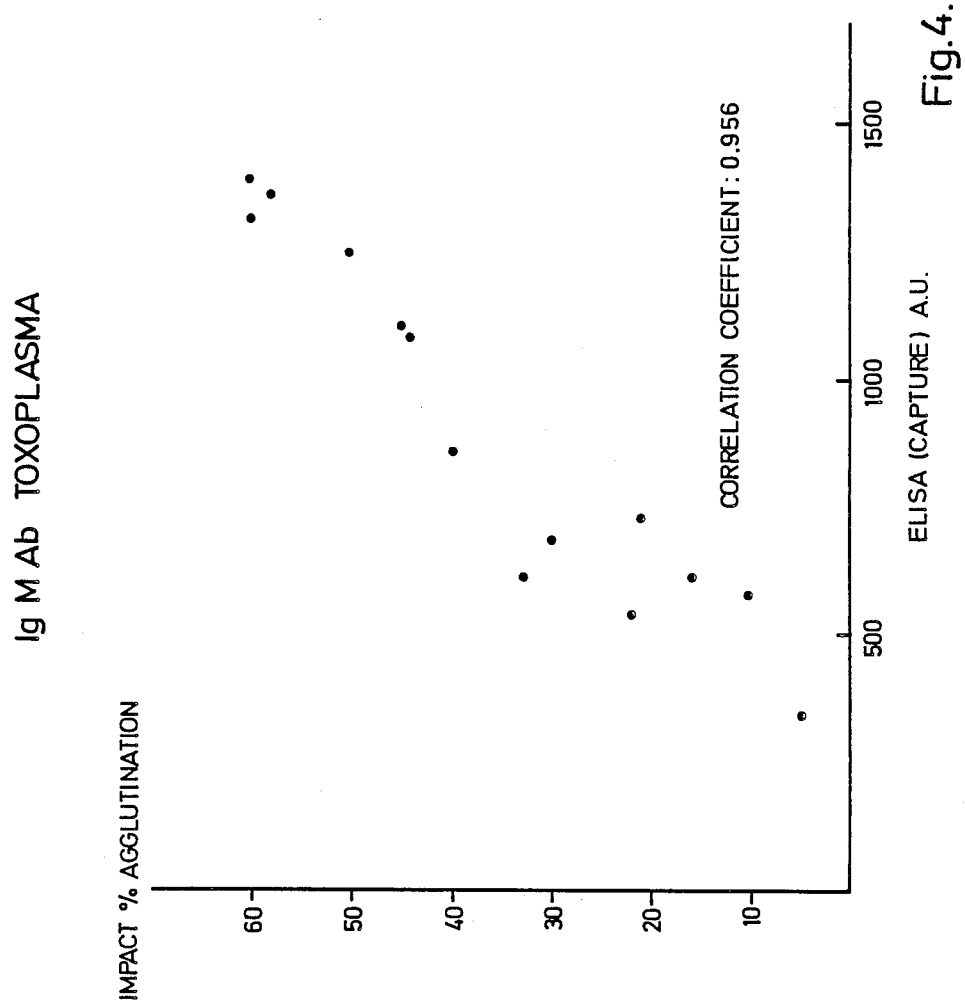

METHOD FOR IMMUNOLOGICAL ASSAY OF ANTIBODIES OF VARIOUS TYPES IN A LIQUID SAMPLE

This invention relates to a method for immunological assay of antibodies of various types against one or more said antigens, and more particularly of IgM antibodies in a liquid sample containing IgM, IgG antibodies and possibly other types, such as IgA, IgD, IgE, such as a biological fluid.

When a person is infected by a bacterium or a virus, he develops antibodies, generally of various types, to destroy infectious agents.

Initially, antibodies are mainly of the IgM type but gradually IgG predominate and may persist over many years. Hence simply to determine whether antibodies exist is frequently not useful in diagnosing an infection, although it may be of considerable value in determining whether the person has an immunity, or a resistance to a particular type of infection. If, however, the antibody which is first formed is detected, i.e., IgM, its relative concentration compared to IgG is estimated, it is possible to know whether the infection is recent or old. Such estimations are extremely important during the early pregnancy stages when, for example, various bacterial, protozoal and viral infections can have reached the foetus.

A difficulty with this estimation is the difference between the concentration of IgG and IgM. In terms of molecular concentration, it may be expected that there are, for example 10 more times of IgG present in the human serum than IgM. One may expect that the proportion of IgM or IgG antibodies consisting normally of less than 2% of total IgM or IgG, will be the same for both immunoglobulins.

Many methods described in the literature allows to differentiate IgM antibodies from IgG (Chantler and Diment, Current status of specific IgM antibody assays [1981], 417, in Immunoassays for the 80's, M.T.P. Press Limited, Lancaster, U.K.).

All methods with the exception of the red blood cell agglutination process (Coombs et al. Lancet [1968], 2, 1115) rely on either an antigen or antibody bound to the walls of a tube or well of a microtitration plate to selectively absorb the selected antibody. The tubes or wells are washed to remove any interference caused by the unwanted immunoglobulins or other potential interferants, and a method of marking the IgM (or IgG) antibody is then used to quantify the antibody being measured (see, for example, description by Organon Teknika, Oss, Holland, of their "Toxonostika ® IgM & IgG Microelisa" system). Such methods require many manual steps, a physical separation of bound antibodies from those not bound, washings and long incubation times. A major interferant in most assays is the antibody called "rheumatoid factor" or "RF" which is an IgM that binds to any IgG which has reacted with a polyvalent antigen or which has been aggregated by physical or chemical processes, and which occurs in large proportions in all samples. Furthermore, many tests are only semi-quantitative, namely the results may not be expressed in weight amounts.

Consequently, the object of this invention consists of remedying the above-mentioned drawbacks of the known assay methods, and of providing a method for immunological assay of IgM antibodies in a liquid sample containing IgM, IgG antibodies and possibly other types, such as IgA, IgD, IgE, against at least one said antigen, such as a biological fluid, in an extremely rapid manner, which requires not more than 60 minutes and which is quantitative. The method of the invention does not require any physical separation of IgM antibodies from IgG antibodies or from the serum or body fluid from which the measure is made. Moreover, the same technique allows to measure, for example, the amount of non-IgM antibodies in a liquid sample containing IgM antibodies and other types. Contrary to the other techniques, the method according to the present invention can also be fully automated.

To this end, according to the invention, the liquid sample containing IgM, IgG antibodies and possibly other types, such as IgA, IgD, IgE, against at least one said antigen is reacted with antibodies against IgG and with antibodies against IgA in the case when said sample contains IgA antibodies against one said antigen (IgD and IgE antibodies are generally in a negligible amount). The said antigen bound to finely divided particles, such as, for example red blood cell (usually ranging from 6 to 8 $\mu$m in diameter but may be as small as 5.5 $\mu$m and as large as 9.5 $\mu$m in normal blood) or latex particles, and a free said antigen of the same type as the bound antigen are added to the reaction product so obtained, and the agglutination or non-agglutination extent of these finely divided particles is determined, the amount of IgM antibodies being inversely proportional to the amount of said unagglutinated finely divided particles.

According to a particular embodiment of the invention method, after having added the antibodies against IgG and possibly the antibodies against IgA and after having incubated the so obtained solution, aggregated IgG are added thereto so as to neutralize the effect caused by the rheumatoid factor and so to prevent a reinforcement of the agglutination by IgG antibodies which would not have been completely neutralized by the anti-IgG antibodies and the free antigen.

According to a particular embodiment of the invention, the amount of agglutinated or unagglutinated finely divided particles is determined in the resulting suspension by measuring the nephelometric or turbidimetric effect thereof, or by counting the particles which are agglutinated or unagglutinated.

The invention also relates to a method for immunological assay of IgG+IgA antibodies in a liquid sample containing IgM, IgG and IgA antibodies, such as a biological fluid, wherein first the amount of IgM antibodies in the liquid sample is determined by means of the above-mentioned method, and wherein then the so obtained amount of IgM antibodies is subtracted from the total amount of IgM+IgG+IgA antibodies, so as to obtain the amount of IgG+IgA antibodies, the quantity of total antibody activity being based, for example, on the principle of agglutination by the antibodies of latex coated with the antigen, and of counting agglutinated particles, such as has been described in many publications (for example, Masson et al. Particle Counting ImmunoAssay (PACIA) in Methods in Enzymology [1981] 74, 106 Academic Press).

The feature of the process of this invention is to restrict the agglutinating activity to IgM antibodies and thereby to use the established agglutination technique to accurately estimate the presence of said IgM antibodies in the presence of other antibodies, namely IgG and possibly IgA. As it is well known, when latex "Lx" is coated with an antigen "Ag" (deriving, for example, from the bacterium or virus causing the illness giving rise to the antibody) and the LxAg is passed through a cell counter, it will give a peak proportional to the concentration of single LxAg particles. When antibodies of the IgM class (IgMA$_b$) are brought into contact with LxAg, these antibodies will cause some LxAg agglutination, decreasing the number of free LxAg particles and hence decreasing their concentration. This decrease is directly proportional to the total antibody quantity (IgGA$_b$ and IgMA$^b$ and possibly IgAA$_b$) present in the sample being measured.

It seemed logical that it would be possible to delete the reaction by IgGA$_b$ by adding a substance which would aggregate the IgGA$^b$ and hence remove them from reacting with the latex, leaving simply the reaction with the IgMA$_b$, as has been described by Gispen et al (Clin. Exp. Immunology. [1975] 22,431) or Schmitz et al (J. Clin. Microbiol. [1975] 1,132).

In the case of the examined liquid sample also containing IgA (IgAA$_b$) antibodies, the latter could also be removed from the reaction with latex by adding a substance which would aggregate them. According to the invention, one selects as a specific reagent to remove the IgG totally an antiserum from a goat directed towards the so-called Fc region of human IgG (anti-Fc) and which is known to aggregate human IgG antibodies selectively. When all IgM antibodies are inactivated by treatment with dithiothreitol (DTT) which does not destroy IgG antibodies, an agglutination of LxAg is still obtained but to a lesser extent. If anti-Fc antibodies are added to this suspension to aggregate the IgG antibodies, no agglutination of LxAg is any longer noted. It is assumed, therefore, that the agglutination of latex by IgG antibodies is inhibited by the antibodies directed against the IgG. Unexpectedly, the LxAg agglutinates more weakly than expected when one adds known relatively high concentrations of IgMA$^b$ (no DTT treatment) to the IgGAb which were aggregated by anti-Fc antibodies, indicating that the Ag antigen on the latex is presumably masked by the IgGA$^b$-anti-Fc complexes. To block the reaction between IgG antibodies and the LxAg antigen, free antigen "Ag" is then added to the suspension. One might assume that such an antigen would also block the IgM antibodies able to agglutinate the latex. Surprisingly, this blocking does not happen if the concentration of free antigen is not excessive. By using free antigen Ag with anti-Fc antibodies to aggregate all the IgG antibodies, the concentration of free particles is apparently the same as when the agglutination is due to IgM antibodies only. This finding although surprising in its effectiveness, is consistent with the known characteristics of both antibodies. The IgMA$^b$ usually have a weaker affinity than the IgGA$_b$. However, because of their multivalency (10 valences), the IgMAb react preferentially with the antigen bearing repeated antigenic determinants. Coupling Ag to latex makes Ag repetitive and therefore highly reactive with the IgMAb. A low concentration of free antigen can therefore saturate the whole binding capacity of IgG antibodies, whereas a very much higher concentration of free Ag, provided it does not contain repetitive antigenic determinants, would be required to saturate IgM antibodies.

Consequently, the process of this invention allows to measure the IgM antibody activity by using, for example anti-Fc antibodies against IgG and obviously antibodies against IgA when the liquid sample being examined comprises IgA antibodies, the IgD and IgE antibodies generally existing in an negligible amount, as already mentioned, and a free antigen, the IgG antibodies in fact combining with the free antigen, this combination with antigen so completing the inactivation of the IgG antibodies and possibly of the IgA antibodies.

The process of the invention also allows, as already mentioned earlier, to assay IgG+IgA antibodies in a liquid sample containing IgM, IgG and IgA antibodies, first by determining the quantity of IgM antibodies in the liquid sample being examined, by the just described process of the invention, and then by subtracting the so obtained amount of IgM antibodies from the total quantity of IgM+IgG+IgA antibodies so as to obtain the quantity of IgG+IgA antibodies. To obtain the amount of IgG antibodies, it will be obviously sufficient to add anti-IgA antibodies to the reaction mixture and, similarly, to obtain the amount of IgA antibodies, it will be sufficient to add anti-IgG antibodies to the reaction mixture.

One problem which has brought many methods of the prior art to lead to falsely positive results has been the interference caused by the rheumatoid factor (RF) which is a IgM antibody binding to most of IgGAb-Ag complexes. According to the invention, the effect of this rheumatoid factor has been neutralized by adding aggregated IgG. The effectiveness of this step was tested by adding a serum containing a very high concentration of rheumatoid factor but devoid of IgMA$^b$, after addition of antibodies against IgG, and possibly antibodies against IgA and incubation of the so obtained mixture. In no case, a substantially different result was obtained.

It has to be noted that a latex agglutination test for the specific determination of IgMA$_b$ has recently been described (J. S. Remington et al. Detection of Immunoglobulin M antibodies with antigen tagged latex particles in an immunosorbent assay. J. Clin. Microbiology. [1983] Vol. 17, No. 5, 939). As with almost all previous tests, antibodies against human IgM antibodies are bound to the walls of the well of a microtitration plate. When serum is added, a proportion of all the IgM adheres to the walls, including IgM antibodies. After this reaction is completed, latex particles coated with antigen are added. After several hours, the amount of latex bound to the microplate is noted and is compared with the results obtained with known concentrations of IgM antibodies and an estimate is so made of the amount of antibodies present. The limitations of this method are that the estimation is only semi-quantitative. The method estimates only IgM antibodies, has long incubation times, requires washing to remove interferants and is work intensive. Furthermore, where the patient has an elevated IgM immunoglobulin level, the proportion of bound IgMA$_b$ will decrease, hence reducing the sensitivity with the danger that positive results may be missed.

To this end, it has to be noted that the incubation periods used in the process of the present invention are of short duration. Thus after having added antibodies against IgG, and possibly antibodies against IgA, the so obtained solution is incubated under stirring at a temperature of about 37° C. for a period of about 1 to 15 minutes. On the other hand, after having added the antigen bound to finely divided particles and the free antigen, the so obtained suspension is also incubated under stirring at a temperature of about 37° C. for a period of about 1 to 15 minutes, a similar incubation appearing as necessary after possible addition of aggregated IgG used for neutralizing the effect caused by the rheumatoid factor.

Although the process of the invention may be applied to any infection, for example of the toxoplasmosis, cytomegalovirus, herpes, rubella type and the like, two embodiments will be described relating to the determination of IgG and IgM antibodies against on the one hand *Brucella abortus* and on the other hand *Toxoplasma gondii*. The Brucella antigen was lipopolysaccharide (LPS).

EXAMPLE 1

Preparation of LPS

Brucella LPS was extracted by means of a water-phenol procedure of Westphal et al. (Method in Carbohydrate Chemistry, Vol. 5, [1965], p. 83, Academic Press, N.Y.). The phenol phase was then precipitated by 3 volumes of "methanol reagent" and treated with dimethylsulfoxide in NaI (5 cycles) as described by Moreno et al. (J. Bacteriology, [1979], 361, 138, No. 2). The lipopolysaccharide (LPS) was then dialyzed against deionized water and lyophilized.

Preparation of latex-antigen (LxLPS)

To 50 μg of LPS dissolved in 0.4 ml of 5-fold diluted GBS (dGBS)(GBS : glycine buffered saline of pH 9.2), 50 μl latex (10% w/v) (K109, Rhone-Poulenc, Courbevoie, France) was added and the mixture was sonicated for 1 minute at 30 Watts (Model B12 Sonifler, Branson, Danbury, Conn., 06810). After 10 minutes 100 μg of human serum albumin (HSA, Behringwerke, Marburg/Lahn, FRG) in GBS was added, and the suspension was sonicated again. After 20 minutes of incubation at room temperature and centrifugation for 10 minutes at 10,000 rev/min in a SS 34 rotor of a Sorvall R5 CB centrifuge, the latex was resuspended in 1 ml of aqueous sodium dodecyl sulfate solution, sonicated and incubated for 1 h at 37° C. The latex was then washed twice with 1 ml of GBS and resuspended in 1 ml of EDTA (ethylene diamine tetraacetate) - GBS-BSA (bovine serum albumin). The latex stored frozen at −20° C. or lyophilized was found to be stable for at least 6 months. LxLPS which has been thawed or resuspended after lyophilization was sonicated for 15 seconds at 30 Watts. Before use, LxLPS was diluted 100 times in EDTA-GBS-BSA.

Anti-Fc antibodies

The Fc fragment of human IgG was prepared by papain digestion according to the method of Cerottini et al (J. Immunology, [1968] 101, 433). 100 μg of human Fc in complete Freund's adjuvant was injected intradermally into a goat at 3 week intervals. The serum was collected 15 days after the final injection, immunoglobulins were extracted and used in a diluted state in GBS (1 mgr/ml) after having checked their anti-Fc specificity.

Procedure

To 50 μl of human serum 50:1 diluted with GBS, 25 μl of anti-Fc were added. The mixture was incubated at 37° C. for 2 minutes with vortexing. 25 μl of aggregated human IgG immunoglobulins at a concentration of 25 mg/ml were then added and the mixture was further incubated for 10 minutes at 37° C. Finally, to this mixture 25 μl of LxLPS mixed with free antigen (LPS) at a concentration of 5 μg/ml was added, and incubation was continued for further 10 minutes at 37° C. The reaction was stopped by the addition of 2 ml of GBS and the resulting mixture was then passed through an optical cell counter where the concentration of unagglutinated LxLPS was determined. The concentration of IgM antibodies was inversely proportional to the concentration of free latex particles. Obviously, one could also directly measure the amount of agglutinated LxLPS or use for counting another method than optical, for example counting of particles by electrical resistors. To avoid errors due to an excessive concentration of IgM antibodies, the procedure is repeated with 100/1 and 200/1 diluted serum.

According to a variant, the agglutination of latex may be measured turbidimetrically when concentrations of IgM and IgG antibodies are relatively high. The same quantities of human serum in GBS and of anti-Fc were incubated for 2 minutes at 37° C. with vortexing. 25 μl of aggregated human IgG at the above concentration was then added and the mixture was allowed to incubate for one hour, after which time 30 μl of LxLPS at a concentration of 0.02% was added. The mixture was briefly vortexed and the turbidity was measured at 620 nm and at 405 nm, the wavelength of 620 nm establishing the baseline. The mixture was then allowed to incubate for two hours, after which the turbidimetric effect of the latter was measured a second time at the above two wavelengths. The decrease in the difference between the measurements at 620 nm and 405 nm initially and those taken after the 2-hour incubation is inversely proportional to the remaining free particles. The amount of agglutinated or unagglutinated finely divided particles in the resulting suspension could also be determined by other optical density measures than turbidimetry, such as nephelometry.

Concerning the assay of total antibody activity, namely of the activity of IgM+IgG antibodies (the serum such as examplified hereinabove containing no IgA antibody), GBS buffer is used alone instead of anti-Fc antibodies and LxLPS instead of LxLPS+LPS. To determine the IgG antibodies concentration alone, the same procedure is used as for determining the total antibody activity, with the exception that IgM antibodies of the sample are destroyed by pretreating this sample with dithiothreitol (DTT).

To 50 μl of serum before dilution with GBS, 170 μl of EDTA at a 50 millimolar concentration in GBS, pH 9.2, was added. To this mixture, 15 μl of DTT in water at a concentration of 10 mg/ml was added and the entire mixture was then incubated at 37° C. for 30 minutes, after which the reaction of DTT was stopped by addition of 15 μl of a 0.2% hydrogen peroxide solution. One proceeded then as hereinabove described and the obtained solution was diluted at 1/10, 1/20 and 1/40 for the above assays.

FIG. 1 enclosed shows the IgM antibody concentrations of the same serum of a patient who was infected with *Brucella abortus*, said concentrations having been obtained by the radio-immunoassay (RIA) method (in counts per minute) and by the process of the invention (in arbitrary agglutination units) for a period for one year.

As it may be noted, both curves are similar, which proves that the assay process of the invention is reliable.

EXAMPLE 2

Measurement of IgG and IgM toxoplasmosis antibodies

Preparation of toxoplasmosis antigen (toxoantigen)

The toxoplasmosis antigen was prepared from the peritoneal exudate of mice infected three days previously with trophozoites of *T. gondii*. The peritoneal cavity was washed two to three times with 3-5 ml of sterile physiological saline and the washings were then pooled. To 1 ml of this suspension, 0.05 ml of the antibiotic Pentrexyl and 10 units of heparin were added and allowed it to stand for ½ hour at room temperature in tubes with conical bottoms. The tubes were then centrifuged for 4 minutes at 600 rpm, the supernatant was removed, the pellet resuspended in saline and again centrifuged for ½ hour at 4,000 rpm at 4° C. After adding to the pellet 2 ml of 1M NH4Cl to hemolyse the red cells, and centrifuging again at 4,000 rpm at 4° C., the pellet was washed three times with saline and centrifuged again for ½ hour at 4,000 rpm at 4° C.

The pellet was resuspended in 2 ml of distilled water and then repeatedly frozen with dry ice acetone and thawed, each time the solution being subjected to ultrasonic mixing. After centrifuging for 10 minutes at 3,000 rpm, the supernatant was removed and passed through a column of Ultrogel 3-4 equilibrated with PBS-NaCl (1M). The fractions were tested against latex-F(ab')2 anti-toxoplasmosis and those fractions which agglutinated latex were pooled, concentrated and stored at −20° C.

Preparation of latex-toxoantigen (Lxtoxo)

To 250 μl of carboxylated latex (10% w/v) (Lx), 2 ml of barbitol buffered saline (BBS) (0.02M, pH 8.1) was added and centrifuged for 10 minutes at 10,000 rpm. Supernatant was removed, and 250 μl BBS was added and cooled to 4° C. 250 μl of BBS containing 25 mg of carbodiimide (CDI) to yield a mixture of 10 mg CDI/100 μl Lx was then added, the solution being freshly prepared and kept at 4° C. and incubated for 1 hour with vortexing at 4° C.

After centrifuging at 4° C. for 10 minutes at 10,000 rpm, 0.5 ml of cold BBS was added. While the mixture was in an ice bath, it was subjected to ultrasonic vibration and added to the solution of toxoantigen (1.5 mg) in BBS at 4° C. (volume±0.5 ml).

The solution was then incubated at 4° C. for 2-4 hours under vortex or for 16 hours on a roller.

The latex suspension was washed 3 times with 1% GBS and ultrasonic mixed each time after centrifugation.

Storage: Diluted 1/20, frozen or lyophilized.

Anti-Fc antibodies

The Fc fragment of human IgG was prepared by papain digestion according to the method of Cerottini et al (J. Immunology. [1968] 101, 433). 100 μg of human Fc in complete Freund's adjuvant was injected intradermally into a goat at 3 weeks intervals. The serum was collected 15 days after the final injection, immunoglobulins were extracted and used in 0.9% saline (12 mg/ml) after having checked their anti-Fc specificity.

Procedure

To 50 μl samples of human sera, diluted 50/1 (or 25/1) in GBS/1% BSA, 25 μl of anti-Fc solution (12 mg/ml in 0.9% saline) was added and allowed to incubate for 10 minutes at 37° C. To this mixture was then added 25 μl of a solution of aggregated human IgG (by heating IgG for 30 minutes at 63° C.) at a concentration of 10 mg/ml in 0.9% saline and again incubated at 37° C. for 10 minutes. Finally, 50 μl of Lxtoxo containing free toxoplasmosis antigen at a concentration of 0.1 μg/ml was added. Incubation was continued for another 30 minutes at 37° C. and the reaction stopped by the addition of 2.0 ml of GBS. The resulting mixture was passed throgh an optical cell counter where the unagglutinated latex particles only were counted, their concentration being inversely proportional to the IgM antibodies.

Alternatively, the concentration of free latex particles may be measured turbidimetrically where the concentration IgMAb or IGGAb are relatively high.

The same quantities of human serum in GBS, anti-Fc, were incubated for 2 minutes at 37° C. with vortexing. 25 μl of aggregated human IgG at the above concentration was then added and the mixture allowed to incubate for one hour, after which time 30 μl of Lxtoxo at a concentration of 0.02% was added. The mixture was briefly vortexed and the turbidity was measured at 620 nm and at 405 nm, the 620 nm establishing the baseline. The mixture is then allowed to incubate for two hours, after which the mixture is read a second time at the above two wavelengths. The decrease in the difference between the measurement at 605 nm and 405 nm initially and finally noted is inversely proportional to the free particles remaining.

For the estimation of total antibody activity, GBS buffer alone was used in place of anti-Fc and Lxtoxo was used without free toxoantigen.

In order to estimate IgG antibody only, the same procedure was used as for total antibody except that the IgM of the sample was destroyed by sample pretreatment with dithiothreitol (DTT).

To 50 μl of serum before dilution with GBS, 170 μl of EDTA at a 50 millimolar concentration in GBS, pH 9.2 was added. To this mixture, 15 μl of DTT in water at a concentration of 10 mg/ml was added and the entire mixture was then incubated at 37° C. for 30 minutes, after which the reaction of DTT was stopped by addition of 15 μl of a 0.2% hydrogen peroxide solution. One proceeded then as hereinabove described and the obtained solution was diluted at 1/10, 1/20 and 1/40 for the above assays.

FIG. 4 shows the correlation between IMPACT (Registered trade mark) and ELISA capture techniques for the determination of IgM antibodies against toxoplasmosis. Correlation coefficient=0.96.

Figure 1:
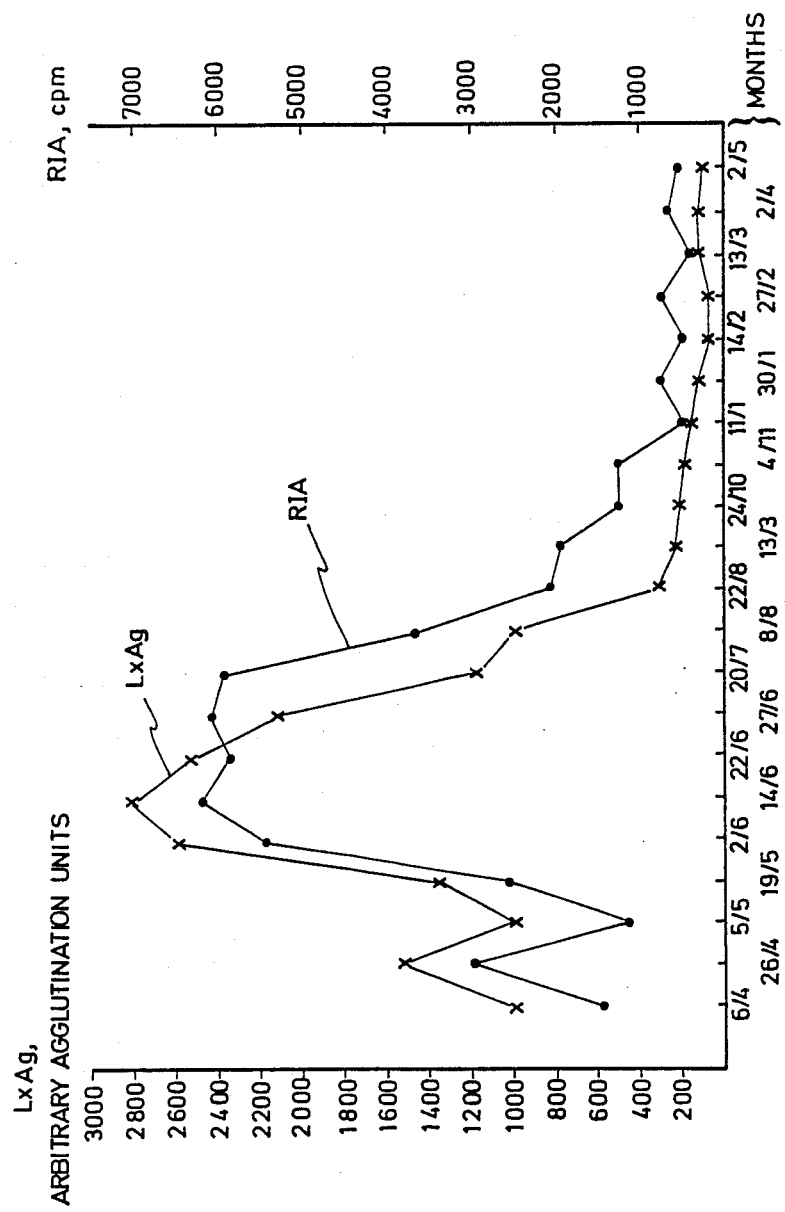
Figure 2:
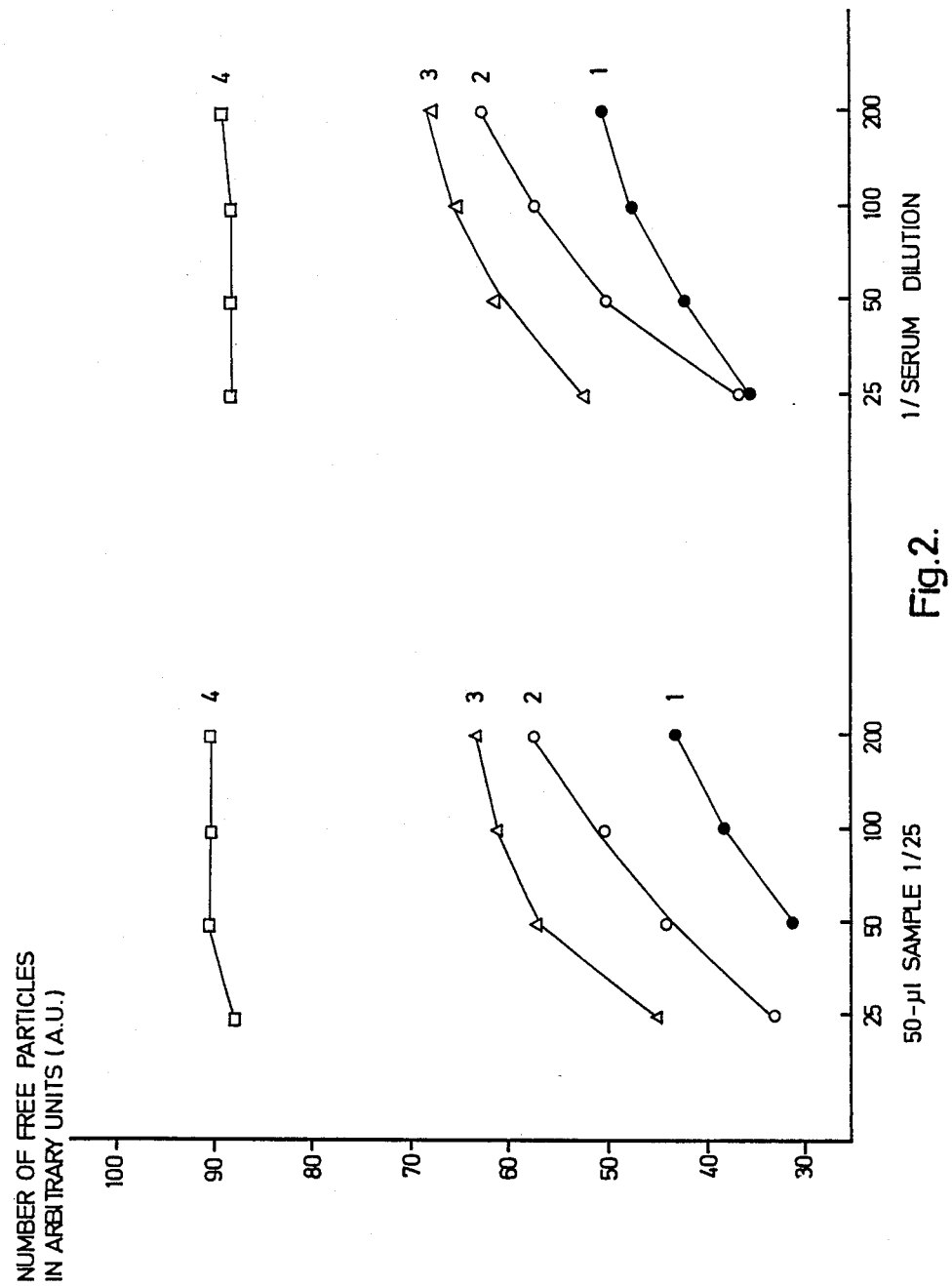
FIG. 2 shows the relative concentrations in 2 sera (1/25 dilution) of IgGAb and IgMAb, i.e. total antibodies (Curve 1), IgGAb (Curve 2), IgMAb (Curve 3) and finally with all antibody activity inhibited by the addition of DTT (against IgM antibodies) and anti-Fc antibody (against IgG antibodies) (Curve 4) as a function of serum dilution.
Figure 3:
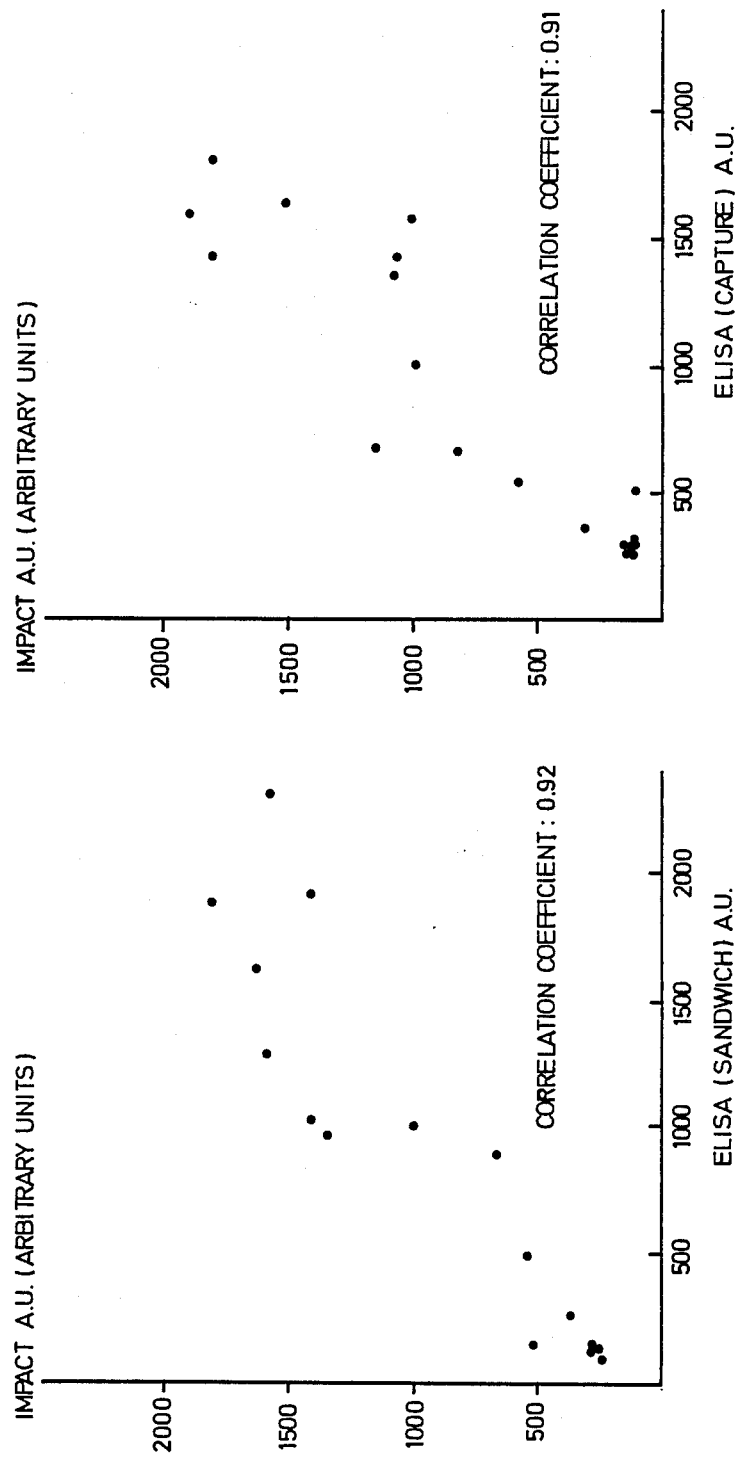
FIG. 3 shows the correlation between the IMPACT (Registered trade mark) system and the determination of IgM antibody against Brucella, compared with results obtained from an ELISA sandwich test and an ELISA capture test. Correlations gave a correlation coefficient of 0.92 for the former and 0.91 for the latter.

It has to be understood that this invention is in no way limited to the hereinabove described embodiments and that many modifications may be brought thereto without departing from the scope of the present patent.

As already mentioned previously, it could be obviously possible to use red blood cells as finely divided particles instead of latex particles.

We claim:

1. A method of immunologically determining an amount of IgM antibodies against at least one antigen in a diluted liquid sample containing IgM and IgG antibodies against said at least one antigen comprising the steps of:
   (i) reacting said liquid sample with antibodies against IgG antibodies so that a reaction product is formed,
   (ii) adding to said reaction product said at least one antigen in a free form and in a form bound to finely divided particles having diameters of less than about 9.5 μm,
   (iii) allowing said particles to agglutinate, and
   (iv) determining the amount of agglutinated or non-agglutinated particles,
   wherein said amount of non-agglutinated particles is inversely proportional to said amount of IgM antibodies.

2. The method according to claim 1 wherein said reacting step (i) comprises stirring said liquid sample with said antibodies against IgG antibodies at a temperature of about 37° C. for about 1–15 minutes.

3. The method according to claim 1 wherein said agglutination step (iii) comprises stirring said reaction product and said at least one antigen in a free form and in a form bound to finely divided particles at a temperature of about 37° C. for about 1–15 minutes.

4. The method according to claim 2 further comprising after said reacting step (i) and before said adding step (ii), adding to said reaction product aggregated IgG antibodies so that a rheumatoid factor effect is neutralized.

5. The method according to claim 4 further comprising stirring said reaction product and said aggregated IgG antibodies at a temperature of about 37° C. for about 1–15 minutes.

6. The method according to claim 1 wherein said amount of agglutinated or non-agglutinated particles is determined by measuring a nephelometric effect thereof.

7. The method according to claim 1 wherein said amount of agglutinated or non-agglutinated particles is determined by measuring a turbidimetric effect thereof.

8. The method according to claim 1 wherein said amount of agglutinated or non-agglutinated particles is determined by counting said agglutinated our non-agglutinated particles.

9. The method according to claim 1 wherein said finely divided particles are latex particles or red blood cells.

10. The method according to claim 1 wherein said antibodies against IgG antibodies are anti-Fc antibodies of IgG and said antigen is a Brucella lipopolysaccharide.

11. The method according to claim 1 wherein said liquid sample is a biological fluid.

12. The method according to claim 1 wherein said liquid sample contains IgA antibodies and wherein said reacting step (i) comprises reacting said liquid sample with antibodies against IgG and IgA antibodies.

13. A method of immunologically determining a combined amount of IgG and IgA antibodies in a diluted liquid sample containing IgM, IgG and IgA antibodies against at least one antigen comprising the steps of:
   (i) reacting said liquid sample with antibodies against IgG and IgA antibodies so that a reaction product is formed,
   (ii) adding to said reaction product said at least one antigen in a free form and in a form bound to finely divided particles having diameters of less than about 9.5 μm,
   (iii) allowing said particles to agglutinate, and
   (iv) determining the amount of agglutinated or non-agglutinated particles,
   wherein said amount of non-agglutinated particles is inversely proportional to said amount of IgM antibodies; and
   subtracting from a combined amount of IgM and IgG and IgA antibodies, said amount of IgM antibodies.

* * * * *